United States Patent [19]

Dennison

[11] Patent Number: 5,157,379
[45] Date of Patent: Oct. 20, 1992

[54] METHOD FOR MONITORING A PROTECTIVE GARMENT

[76] Inventor: Everett Dennison, 200 Glenview, Canfield, Ohio 44406

[21] Appl. No.: 740,093

[22] Filed: Aug. 5, 1991

Related U.S. Application Data

[63] Continuation-in-part of Ser. No. 684,551, Apr. 12, 1991, Pat. No. 5,109,215, which is a continuation-in-part of Ser. No. 537,811, Jun. 14, 1990, Pat. No. 5,036,309.

[51] Int. Cl.$^5$ ............................................. G08B 21/00
[52] U.S. Cl. .................................... 340/540; 128/897; 128/898; 128/917; 128/918; 340/605; 606/34
[58] Field of Search ............... 340/540, 647, 604, 605; 606/34; 128/897, 898, 917, 918

[56] References Cited

U.S. PATENT DOCUMENTS

| | | | |
|---|---|---|---|
| 4,178,589 | 12/1979 | Nunn | 340/573 |
| 4,321,925 | 3/1982 | Hoborn et al. | 606/34 |
| 4,583,039 | 4/1986 | Kolcio | 324/557 |
| 4,692,748 | 9/1987 | Pinsak | 340/573 |
| 4,909,069 | 3/1990 | Albin | 340/605 |
| 4,956,635 | 9/1990 | Langdon | 340/540 |

*Primary Examiner*—Glen R. Swann, III
*Attorney, Agent, or Firm*—Terry M. Gernstein

[57] ABSTRACT

A protective garment, such as a surgeon's glove, is monitored for the occurrence of a breach in that garment. The monitoring is performed using an improved version of the system disclosed in U.S. Pat. Nos. 5,036,309 and 5,109,215. The system is further improved by making the protective garment of one piece with one layer of electrically conductive material and one layer of electrically insulating material, and connecting one of the electrical contacts to the electrically conductive layer. Several forms of the protective garment are disclosed, including a dual layer garment and a triple layer garment. The triple layer garment has two forms, one of which includes an insulating layer sandwiched between two electrically conductive layers, and the other form of which has an electrically conductive layer sandwiched between two insulating layers. The apparatus also includes elements that are used to activate an alarm circuit prior to any breach in the garment reaching a condition in which a portion of the workpiece will contact the worker.

14 Claims, 5 Drawing Sheets

METHOD FOR MONITORING A PROTECTIVE GARMENT

BACKGROUND OF THE INVENTION

The present application is a continuation in part of U.S. patent application Ser. No. 07/684,551, filed on Apr. 12, 1991, now U.S. Pat. No. 5,109,215 (hereinafter referred to as the parent application), that was a continuation in part of Ser. No. 07/537,811, filed on Jun. 14, 1990, now U.S. Pat. No. 5,036,309 (hereinafter referred to as the grandparent application). The disclosures of the parent and grandparent patent applications are incorporated herein by reference.

TECHNICAL FIELD OF THE INVENTION

The present invention relates to the general art of wearing apparel, and to the particular field of protective clothing.

In many industries, a worker may not want any portion of a workpiece to contact any portion of his or her skin. This situation occurs in the chemical industry as well as in several other industries. For this reason, the art contains various examples of protective apparel, such as gloves, aprons, boots, pants, smocks, face shields, gowns and the like.

As more is known of various communicable diseases, more and more workers are using such protective garments in their work. Thus, it is not uncommon to find beauticians or other such workers wearing certain types of protective wearing apparel.

The most notable examples of the use of protective clothing are in the medical and health care field. Thus, nearly all doctors wear some sort of protective apparel when working on a patient. It is also not uncommon for dentists to wear protective gloves, masks, gowns, smocks and pants while performing routine examinations and dental procedures. The use of such protection is not limited to doctors, for technicians, nurses, emergency personnel, dental hygienists, and veterinarians are but a few examples of those in the medical field who now commonly wear some sort of protective clothing while carrying out their work. This list is merely representative of the many workers who will benefit from the use of protective clothing, and many other types of workers will occur to those skilled in the art based on the teachings of this disclosure.

Of course, anyone involved in any way with laboratory work in many fields, especially the medical field, almost always wears some sort of protective clothing.

The surgeon and other operating room and hospital personnel are the most visible examples of medical personnel who wear protective clothing while working. Not only do such personnel wear protective clothing to protect a patient from contamination, with the advent of diseases such as hepatitis, AIDS and the like, many such medical workers wear protective clothing to protect themselves from contamination.

While the integrity of all such protective garments must be ensured, the surgical glove has received much attention in the art. One study has found that as much as fifty-nine percent of tested surgical gloves developed leaks when tested every fifteen minutes during surgery, and leakage occurred twenty-five percent of the time when two pairs of gloves were worn. This leakage is probably even higher for certain operations, such as orthopaedic surgery, or the like. Any leakage of the surgical gloves can prove to be dangerous, and should be determined on a regular basis so the medical personnel can be warned upon the occurrence of such a breach.

Therefore, the art has included various procedures which are intended to protect the integrity of the worker's gloves, especially surgical gloves. These procedures have included requirements for a worker to change his gloves at a regular interval, or which require a worker to wear several pairs of gloves. Such procedures are not entirely successful because they interrupt the worker from his work and break his concentration. Furthermore, wearing several pairs of gloves may interfere with proper performance of the task. Even then, as the above-mentioned study found, the worker may not be fully protected.

Thus, the art has also included devices and systems which are intended to detect breaches in a worker's gloves. One such system is disclosed in U.S. Pat. No. 4,321,925. The device disclosed in this patent is intended to continuously monitor a surgeon's gloves to warn of any perforations in those gloves. This device includes a contact on the patient, a contact on the surgeon, and an electrical path through the doctor's shoe, and through the operating room floor to and through the base of the operating table and to and through the table.

While this device overcomes some of the above-mentioned problems, it still has several drawbacks which were discussed in the parent application.

While ensuring the integrity of a worker's gloves is quite important, due to the highly contagious and dangerous nature of many diseases and many chemicals, integrity monitoring of a workers's gloves alone may not be sufficient protection. In many situations, including a surgical operating room, any physical contact with the workpiece may prove to be dangerous.

Therefore, even beyond the drawbacks and problems mentioned for the known glove testers per se, they may have shortcomings in that they do not monitor all of the protective clothing being worn by a worker. Should that worker have a breach in his or her face mask, for example, such breach can be dangerous if the worker must bring his or her face in close proximity to a patient, for example to perform the work, as might be the case of an ambulance worker who must find and grasp a patient's tongue to prevent choking.

Yet another system for monitoring personnel barriers, such as surgical gloves, is disclosed in U.S. Pat. No. 4,956,635. This system includes a pair of comparitors to monitor the integrity of a barrier. This system monitors probes mounted on the doctor and probes mounted on both the doctor and on the patient. A blinking light indicates that the probes are mounted on the doctor, and a steady light indicates that a breach through the doctor's glove has occurred. The status signal of the system is continuously monitored by the health care worker.

While this system is somewhat successful in overcoming some of the problems associated with protective gloves, it still suffers from several drawbacks which were discussed in the parent patent application.

Both the parent and the grandparent patent applications disclose systems for continuously monitoring protective clothing to detect any breach in such clothing immediately upon occurrence of such breach. These systems achieve this goal, yet even such systems can be improved.

Specifically, these systems can be improved by making them more desirable for a worker to use. For example, the systems disclosed in the parent and grandparent patent applications include electrical contacts that are attached to the worker and to the workpiece, and are connected to an alarm circuit by line conductors. Some workers, especially surgeons, may find such line conductors somewhat inhibiting, or annoying.

While the systems disclosed in the parent and grandparent patent applications are extremely accurate and rapid in response, there is still room for further improvement. These systems have the contacts thereof connected to the worker at one location, such as on his ankle, and to the workpiece at a location, such as at a patient's ankle. Such connection can become loose (and thus the parent patent application discloses a monitoring system for signalling when such event has occurred), and can have the overall results thereof altered by changes in impedance occurring between the contact and the worker or workpiece or even in the worker and/or in the workpiece itself. These systems utilize a current generating element, such as a transistor, to activate an alarm circuit when electrical contact is made between the worker and the workpiece (or some portion of the workpiece). The calibration of the current generating element therefore generally includes factors for the impedance existing in the worker or in the workpiece. If this impedance is known to an exact degree, the design of the overall circuit might be improved. While such impedance is known, the more exact such knowledge is, the more accurate and precise the overall system can be.

Furthermore, if the contacts can be located in positions relative to the worker, to the workpiece and relative to each other that is most effective, the overall performance of the system might be improved. This might be especially helpful in detecting extremely small breaches in the clothing that might involve extremely small amounts of material penetrating the clothing.

Still further, the above-discussed systems require the contact between some portion of the worker and some portion of the workpiece before the alarm is actuated. While this contact can be quite minimal, the systems could be further improved if the alarm could be actuated before any portion of the workpiece contacts the worker. This improvement will further protect the worker.

Therefore, there is a need for a system that monitors the integrity of a protective garment which is a further improvement of the systems disclosed in the parent and the grandparent patent applications. Specifically, there is a need for such an improved system that is less bothersome to wear, can be designed in an manner that might be more accurate in some instances, and can locate the sensing contacts in the most desirable position, and can be adapted to signal the occurrence of a breach before that breach opens a path between the worker and a portion of the workpiece.

OBJECTS OF THE INVENTION

It is a main object of the present invention to provide a system for monitoring the integrity of protective clothing worn by a worker.

It is another object of the present invention to improve the system for monitoring the integrity of protective clothing worn by a worker as disclosed in the parent and grandparent patent applications.

It is another object of the present invention to provide a system for monitoring the integrity of protective clothing worn by a worker and signalling when in that protective clothing is about to be breached, prior to a breach exposing the worker to any portion of a workpiece.

SUMMARY OF THE INVENTION

These, and other, objects are achieved by making a protective garment one-piece and including at least two layers, one electrically conductive layer and one electrically insulating layer, and then having one of the alarm system electrical contacts in the systems disclosed in the parent and/or grandparent applications electrically fixed to the electrically conductive layer of the garment. The other electrical contact of the alarm system is either electrically fixed to the worker or to another electrically conductive layer of the one-piece garment. The electrically insulating layer is electrically interposed between the electrically conductive layer and the worker's body to electrically separate the electrically conductive layer, and the first electrical contact of the alarm system, from the worker. It is understood that the term "conductive layer" is used herein as an example of the many forms of conductive layers that can be used in conjunction with the system of the present invention. Therefore, while the conductive layer can be some form of material, it can also be a conductive coating, an impregnated surface or the like. Thus, the term "conductive layer" is not intended to be limited to the exact forms shown herein.

Both of the electrical contacts are connected to an alarm circuit such as disclosed in the parent and grandparent patent applications. This circuit includes a current generating means that is biased to be in the cutoff state when the protective garment is unbreached; and to be in the active or saturated state should any breach occur in the protective clothing. Alarm elements, such as audible and/or visible elements, are activated when the current generating element is in the active or saturated state.

One specific form of the system embodying the present invention includes a one-piece garment having two layers, one electrically conductive layer in which one contact of the alarm circuit is located, and an electrically insulating layer interpositioned between the conductive layer and the worker. A second contact of the alarm circuit is connected to the worker. Any breach in the garment provides a path through which material, such as bodily fluid from a patient, may pass. This material will bridge the contacts by connecting the electrically conductive layer to the worker. This bridging of the contacts will activate the alarm circuit. Since the insulating layer is extremely thin, the bridge can be extremely small. It is noted that the term "material" in relation to the workpiece or in relation to the protective garment can include any migrating electrically conductive material that is capable of bridging a gap.

Another form of the invention includes a one-piece garment having three layers. In one form of this tri-layer garment, two layers are electrically conductive with an electrically insulating layer sandwiched therebetween. One of the conductive layers is located adjacent to the worker. The contacts of the alarm circuit are electrically connected to the conductive layers. Another form of this tri-layer embodiment includes two insulating layers having a conductive layer sandwiched therebetween. One contact is included in the conductive layer and the other contact is connected to the worker.

In this manner, the electrical contacts can be located directly on the protective garment at a spacing and location that are precisely determined to activate the alarm even when extremely small breaches in the garment appear. Biasing and design of the current generating element can be precise, and the results will be repeatable and accurate. Still further, any elements that may alter the impedance in the overall alarm circuit can be avoided by locating the contacts directly in the garment.

In the case of the tri-layer garment having two electrically conductive layers, the alarm system contacts can be connected to the layers. As soon as the outer layer and the insulating layer are breached, but before the inner electrically conductive layer is breached, the alarm will be activated. The inner conductive layer can still be intact and impermeable to liquid, thereby protecting the worker from contact with the workpiece while the alarm is being activated. Such a situation will be termed identifying an "incipient breach" since the breach in the garment will not totally expose the worker to the workpiece as the inner conductive layer will still be protecting that worker yet the breach will be large enough to activate the alarm. Detecting an incipient breach adds further protection to the garment.

Yet another result of utilizing a one-piece protective garment with at least one electrically conductive layer and at least one electrically insulating layer is the ability to package the entire monitoring system in a small housing that can be located out of the worker's way. An example of such packaging is a package connected to a surgeon's sleeve or having wires leading up that surgeon's sleeve to an alarm housing located in the surgeon's pocket.

BRIEF DESCRIPTION OF THE DRAWING FIGURES

DETAILED DESCRIPTION OF THE PREFERRED EMBODIMENT OF THE INVENTION

Figure 1A:
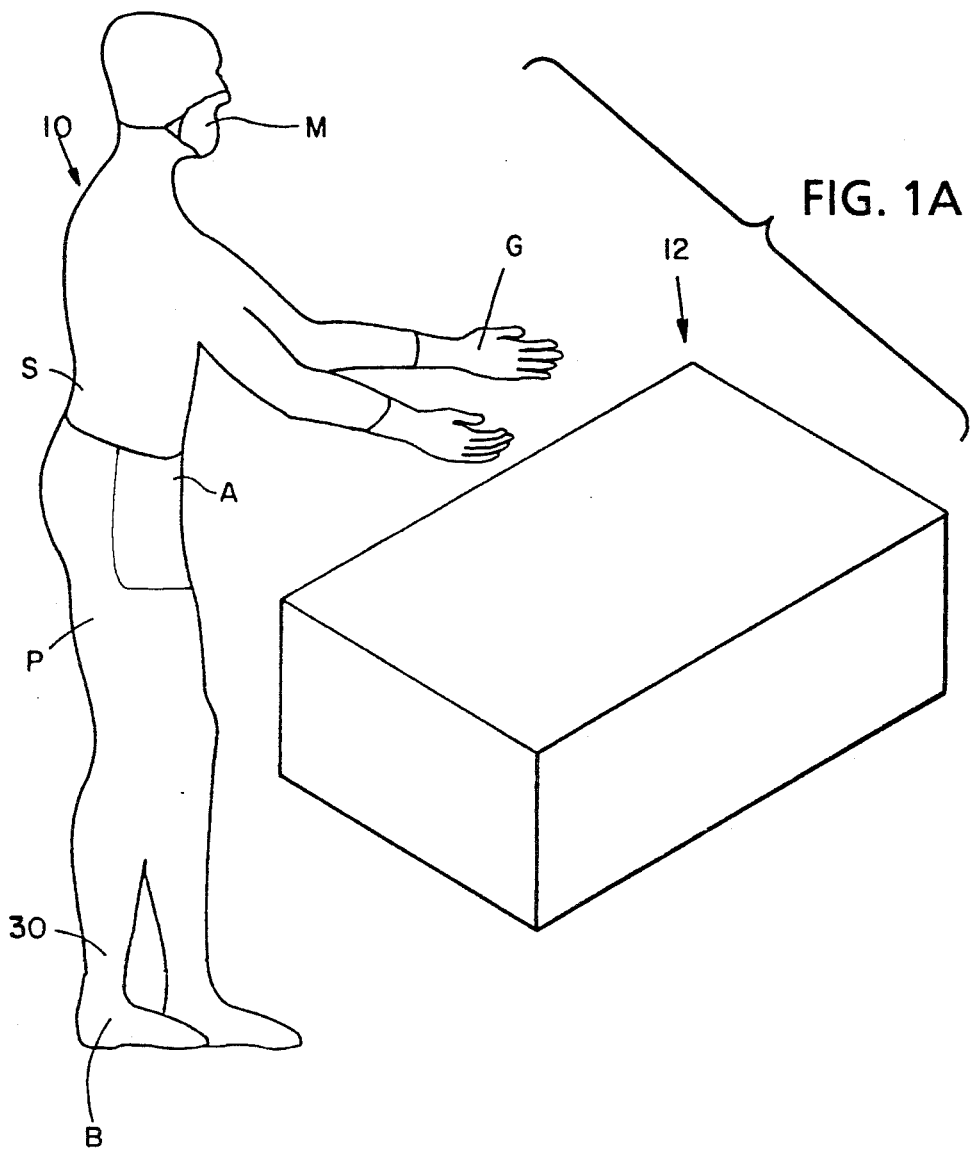
FIG. 1A illustrates a worker in conjunction with a workpiece, with the worker wearing several forms of protective garments.

Shown in FIG. 1A is a worker 10 carrying out a procedure on a workpiece 12. The workpiece 12 is shown in general block form as it can be an inanimate object, such as a chemical or biological experiment, a quality control operation or the like, as well as an animate object such as a human or an animal. Various applications will occur to those skilled in the art based on the teaching of the present disclosure, and thus the specific examples provided herein are not intended to be limiting, but only examples.

Figure 1B:
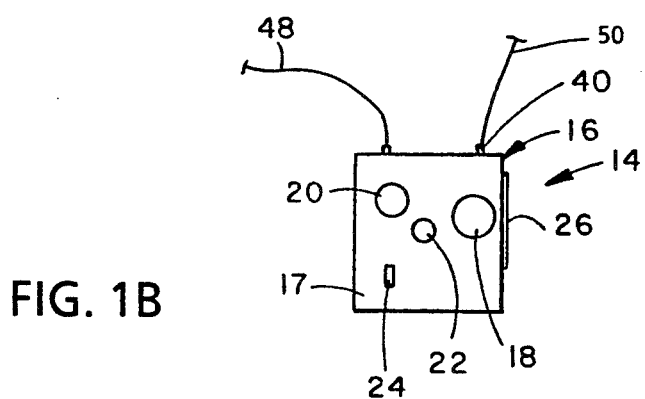
FIG. 1B illustrates a device for monitoring a protective garment worn by a worker.

A system 14 is shown in FIG. 1B for monitoring the integrity of the protective garments worn by the worker 10. The system 14 includes a portable unit 16 having a housing 17 which contains a power source (not shown in FIG. 1B), and various circuit elements connecting that power source to an audible alarm element 18 and/or to a visible alarm element 20. A sensitivity-adjusting element 22 and an 24 on/off switch can be used to connect the power source to the remainder of the circuit. A spring-type clip 26 is mounted on the housing to releasably attach the portable unit to the worker as in his pocket, on his belt or the like. The clip 26 can be replaced by other forms of fastening means, such as VELCRO or the like so the housing can be mounted anywhere that is convenient to the worker.

The worker 10 is shown wearing various items of protective clothing, such as gloves, such as surgical gloves G, boots, such as boot B, a smock or gown S, pants P, an apron A, a face covering such as mask M or the like. As will be understood from the ensuing discussion, the protective clothing worn by the worker is electrically insulating, and prevents electrical contact between the worker and the workpiece. However, should any part of the worker contact any portion of the workpiece in a manner that completes the electrical circuit as via a breach or an incipient breach in that protective clothing, there will be electrical contact between the contact elements of the alarm circuit, thereby completing the circuit and activating the alarm element or elements.

Figure 2B:
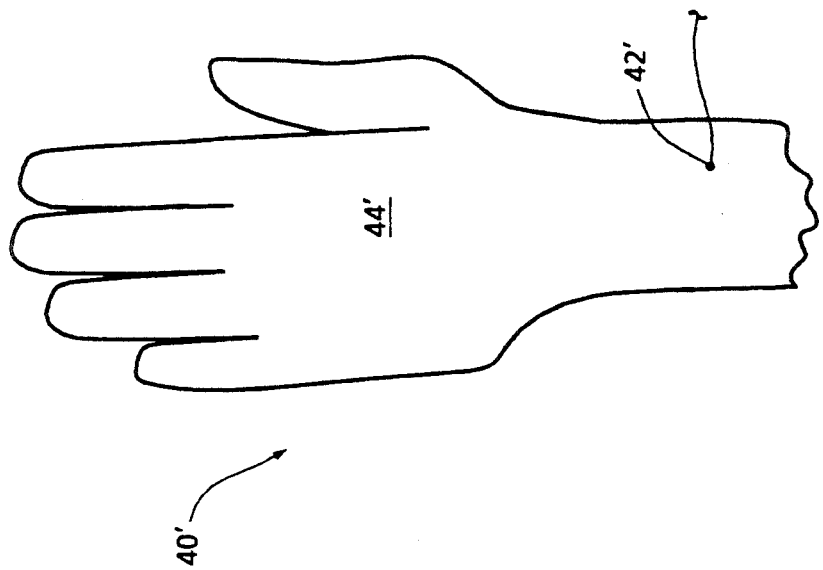
FIG. 2B illustrates another form of the FIG. 2A glove in which an electrical contact of an alarm circuit is integral with the glove.
Figure 2A:
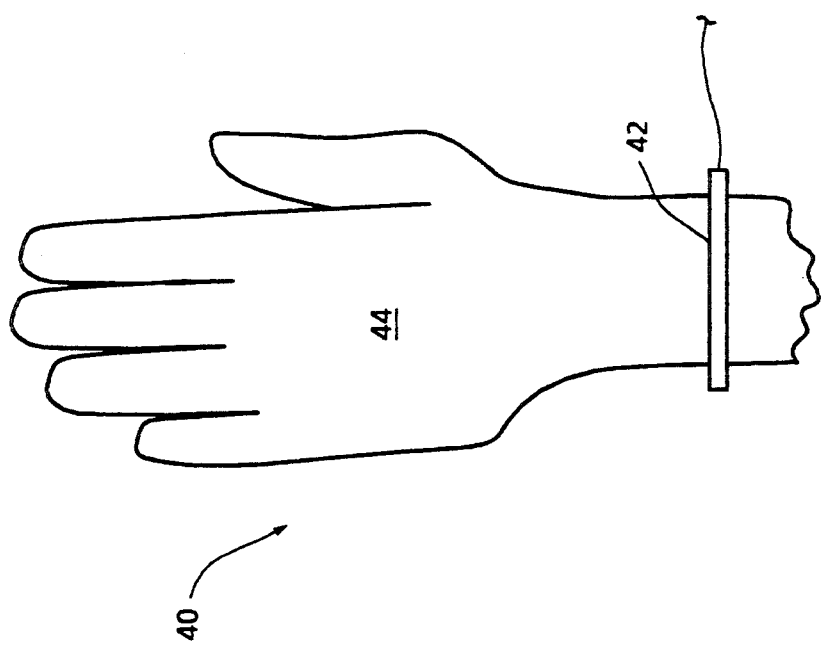
FIG. 2A illustrates a one-piece protective glove embodying a first form of the invention.

One specific form of the present invention is embodied in a glove that is worn by a worker, such as a surgeon or the like. Shown in FIGS. 2A and 2B are two forms of gloves embodying the present invention. It is noted that while a glove is shown and described, no limitation is intended.

Both of the gloves are one-piece in construction and have at least one electrically conductive layer and one electrically insulating layer. The electrically insulating layer is interposed between the electrically conductive layer and the worker. One of the gloves is shown in FIG. 2A as glove 40 and has an electrical contact 42 releasably fixed to an outer surface of the glove outer layer 44. The outer layer 44 is electrically conductive in such an embodiment. In FIG. 2B, a glove 40' has an electrically conductive outer layer 44', and has an electrical contact 42' integral with the outer layer. The contact 42' is shown as a point contact, but will, in fact, encompass the entire outer layer with point 42' merely being the connection between the outer layer and a lead line connected to an alarm circuit. The connection point 42' can include snap fasteners, EKG-type connections or the like.

The various forms of the one-piece protective garment are shown in FIGS. 3A–5B, and attention is now directed to these figures. All of the garment forms are used in conjunction with an alarm circuit 46 and is connected thereto by lead lines 48 and 50. The alarm circuit is similar to the alarm circuits disclosed in the parent and grandparent applications. Accordingly, the disclosures of those alarm circuits are incorporated herein by reference.

Figure 3B:
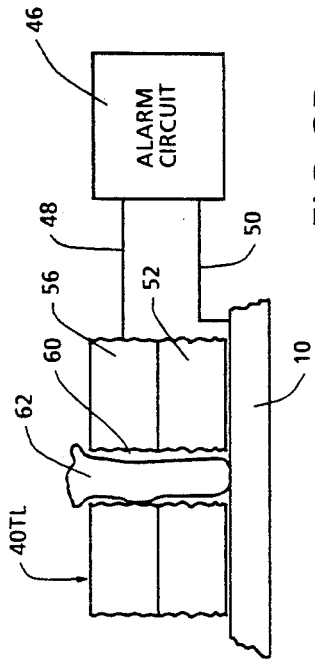
FIG. 3B illustrates the FIG. 3A garment in a breached condition.
Figure 3A:
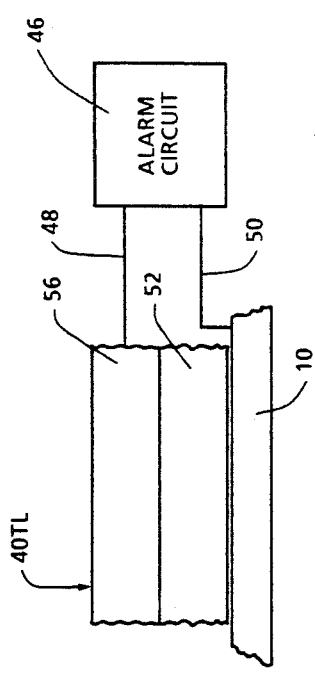
FIG. 3A illustrates a two layer one-piece protective garment in which one contact of an alarm circuit is electrically connected to an electrically conductive layer of the garment and an electrically insulating layer is electrically interposed between the electrically conductive layer and the worker.

A two layer garment 40TL is illustrated in FIGS. 3A and 3B as including an electrically insulating layer 52 located to be adjacent to a worker 10 when the garment is worn, and to be electrically interposed between that worker and an outer layer 56 that is electrically conductive. The alarm circuit 46 has two electrical contacts connected to lead lines 48 and 50, respectively. These contacts are electrically separated by the insulating layer 52 whereby the alarm circuit is open between a power source in that circuit and any alarm elements associated with that circuit.

In most cases, the worker will be working with a workpiece that has some electrical conductivity. For example, body fluids of a patient are electrically conductive. This fact is used by the present invention to close the alarm circuit and activate the alarm elements thereof This feature is illustrated in FIG. 3B where a breach 60 has occurred in the outer and inner layers 56 and 52 respectively. If this breach extends all the way through the garment, it will provide an uninterrupted path between the outer electrically conductive layer and the worker. Such an uninterrupted path will expose the worker to parts of the workpiece, which is to be avoided. Since the workpiece is electrically conductive, any portion of that workpiece, indicated in FIG. 3B by reference indicator 62, will bridge the insulating layer and electrically connect the electrically conductive outer layer to the worker. The electrical contact associated with lead 50 is electrically connected to the worker; therefore, the alarm circuit will be closed as soon as the workpiece portion 62 makes contact with both the outer electrically conductive layer and the worker. This will activate the alarm circuit 46.

Figure 4B:
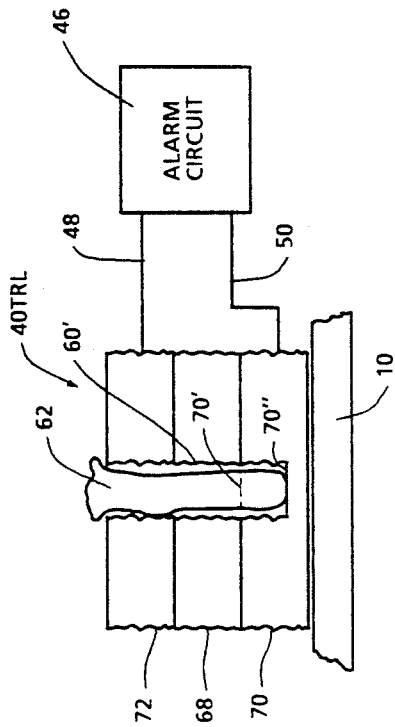
FIG. 4B illustrates the FIG. 4A garment in a breached condition.
Figure 4A:
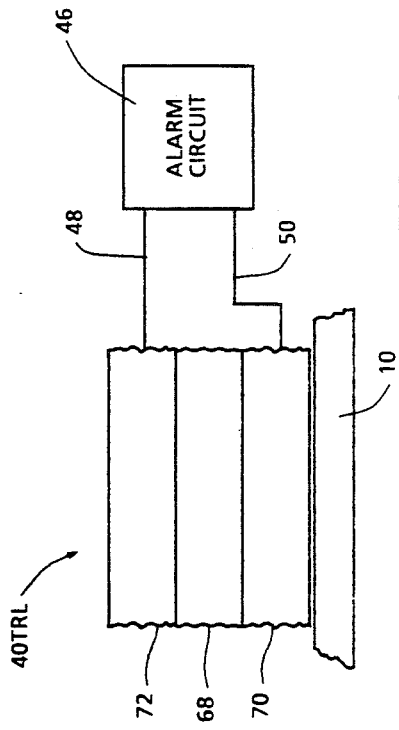
FIG. 4A illustrates a three layer one-piece protective garment having an electrically insulating layer electrically sandwiched between two electrically conductive layers.

Other forms of this garment are indicated in FIGS. 4A–5B, and each of these garment forms operates in a manner similar to the just-described dual layer garment. Each of these garments is one-piece and includes a plurality of layers. For example, a tri-layer garment 40TRL is indicated in FIGS. 4A and 4B in which an electrically insulating layer 68 is sandwiched between an inner electrically conductive layer 70 and an outer electrically conductive layer 72. The contacts associated with the alarm circuit are electrically connected to the electrically conductive layers, either by releasable means or by being integral with the layers.

The inner conductive layer is located adjacent to the worker and is formed of material that is impermeable to the workpiece or portions of that workpiece. This inner layer acts as a protective layer for the garment. As indicated in FIG. 4B, a breach 60' occurring in the garment 49TRL will permit a workpiece portion 62 to penetrate the outer conductive layer as well as the insulating layer. The outer layer 72 will be in contact with the workpiece portion 62. Therefore, as soon as a section of the workpiece portion 62 contacts the inner conductive layer 70, the alarm circuit 46 will be completed, and the alarm elements activated.

The completion of the alarm circuit by workpiece portion 62 bridging the insulating layer and contacting both the inner and the outer conductive layers can occur without the inner layer 70 being completely or even partially breached. This situation is indicated in FIG. 4B by dotted lines 70' and 70" that represent a totally intact inner layer and a partially breached inner layer respectively when the alarm circuit 46 is activated. As can be seen in FIG. 4B, the inner layer 70 will still be preventing contact between the worker and any portion of the workpiece when the alarm is activated. This will warn the worker that, while he is still protected, his protective garment is in danger of being breached. This situation is termed an "incipient breach" condition.

Figure 5B:
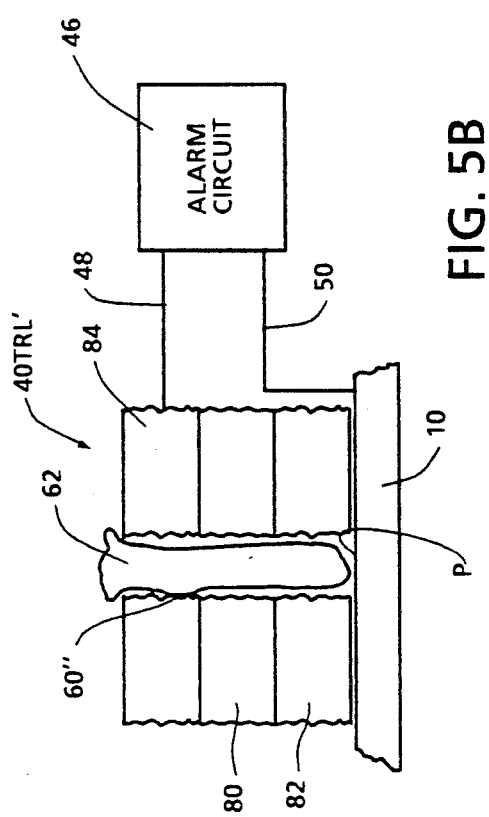
FIG. 5B illustrates the FIG. 5A garment in a breached condition.
Figure 5A:
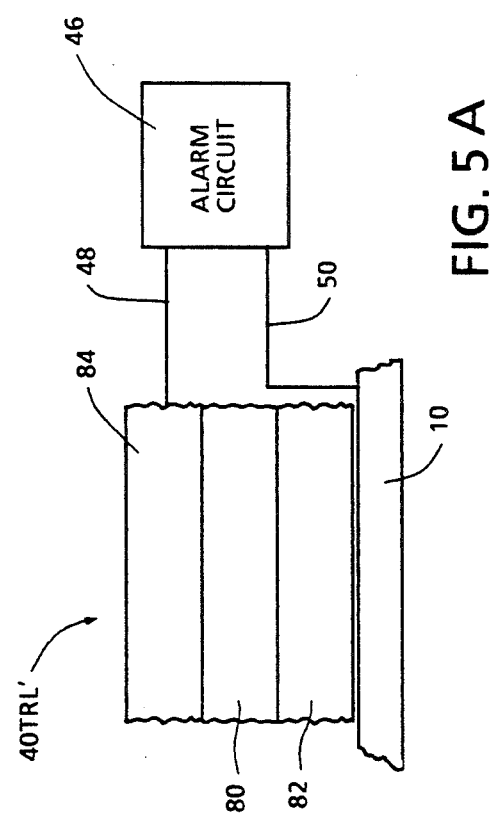
FIG. 5A illustrates a three layer one-piece protective garment having an electrically conducting layer electrically sandwiched between two electrically insulating layers.

A tri-layer protective garment 40TRL' is shown in FIGS. 5A and 5B. The garment 40TRL' is similar to the garment 40TRL, except that the garment 40TRL' has an electrically conductive layer 80 sandwiched between an inner electrically insulating layer 82 and an outer electrically insulating layer 84 with the contacts of the alarm circuit being connected to the conductive layer and to the worker. The breached garment is shown in FIG. 5B in which a breach path 60" has been formed through the three layers and which will expose a portion P of the worker to contact with a workpiece portion 62. As soon as any part of the workpiece portion 62 contacts portion P of the worker, the alarm circuit will be completed and the alarm elements activated.

Figure 6:
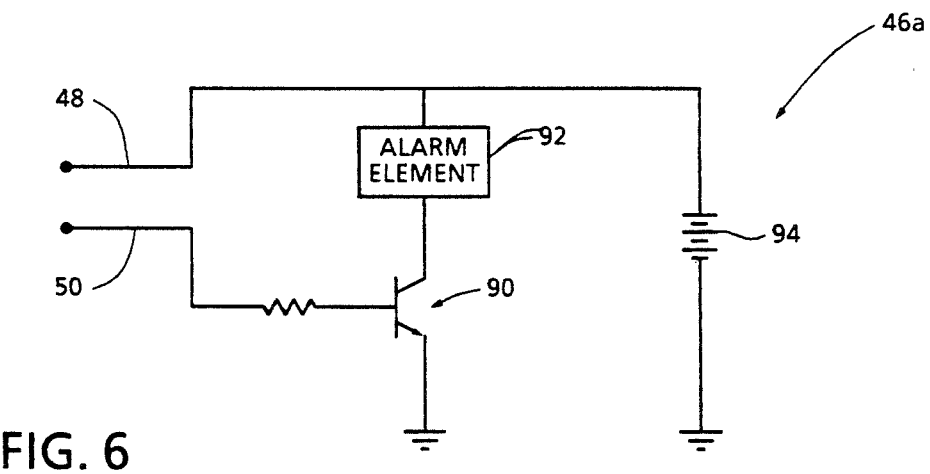
FIG. 6 illustrates a circuit that is suitable for use with the protective garment of the present invention.
Figure 7:
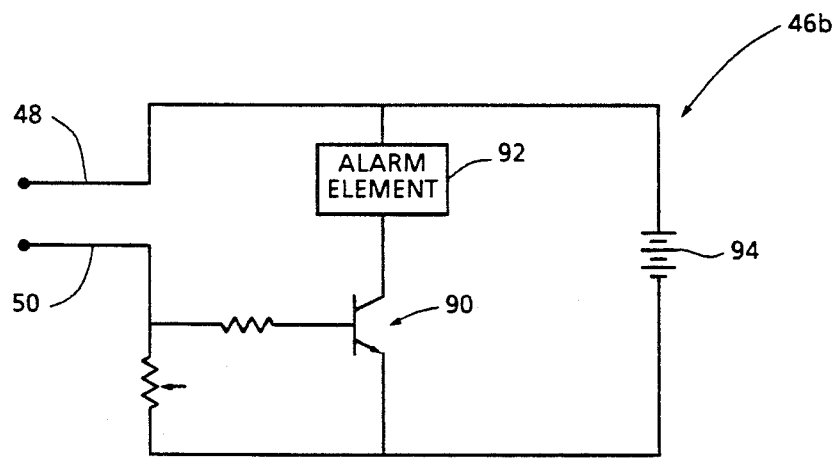
FIG. 7 illustrates a second circuit suitable for use with the protective garment of the present invention.
Figure 8:
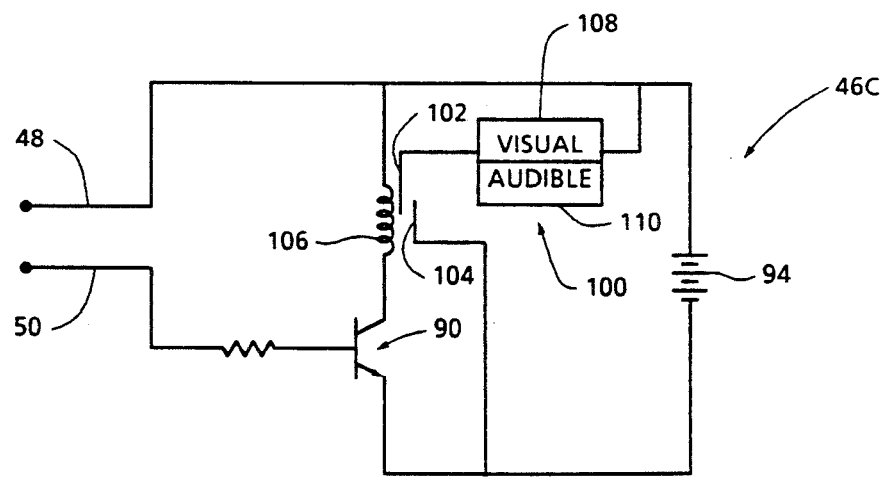
FIG. 8 illustrates yet another circuit suitable for use in conjunction with the protective garment of the present invention.

Three forms of the alarm circuit 46 are shown in FIGS. 6, 7 and 8 as circuits 46a, 46b and 46c respectively. These circuits are identical to the circuits disclosed in the parent and the grandparent applications, and such disclosure is incorporated herein by reference. As shown, each circuit includes a current amplifying element 90 having the base thereof connected to one contact, another portion thereof connected to an alarm element 92 and another portion thereof connected to ground. A power source 94 is also connected to the alarm element. When the contacts associated with lead lines 48 and 50 are electrically separated, the current amplifying element is biased to be in a cutoff state whereby no power is applied to the alarm element. However, as soon as the contacts associated with the lead lines 48 and 50 are electrically connected, the current amplifying element 90 is placed in a saturated or active condition in which power is applied to the alarm element. Such power application will activate that element signalling that something has electrically connected the contacts.

The contacts can be spaced very close together whereby extremely small amounts of the workpiece will activate the alarm elements. In fact, one form of the garment will locate the contacts associated with the leads 48 and 50 at a maximum spacing of 3/64th inch.

An alarm element 100 is shown in FIG. 8 and is one specific form of the alarm element. Alarm element 100 includes a stationary contact 102 adjacent to a movable contact 104. An electromagnet 106 is connected to the current amplifying element 90 to be activated as soon as the circuit is completed by electrical contact between leads 48 and 50. Activation of the electromagnet 106 draws the movable contact toward that electromagnet and into electrical contact with stationary contact 102. Contact 104 is connected to one side of the battery 94 and contact 102 is connected to one side of the alarm elements, such as visible element 108 and audible element 110. The other sides of these alarm elements are connected to the other side of the battery whereby these elements are in parallel and both activated when contact 104 makes electrical contact with contact 102.

Of course all forms of the circuit shown in the parent and grandparent applications can be used in conjunction with the protective garment disclosed herein. The circuits disclosed in the parent and in the grandparent applications, as well as the above-discussed circuits can be adjusted to activate the alarms when resistance between the protective garment and the person wearing that protective garment drops below a specific level. In this manner, the circuits will be used to activate an alarm prior to the protective garment being fully breached. Thus, the partial breaching alarm feature discussed above in reference to FIG. 4B can be achieved using these circuits as well. This provides an important advantage to the apparatus in that a wearer is alerted to a condition that might cause a breach before a breach occurs. The wearer is thus protected and can change the protective clothing prior to any portion of the workpiece contacting his or her body. This feature of the invention is a pre-breach alarm activating means.

It is understood that while certain forms of the present invention have been illustrated and described herein, it is not to be limited to the specific forms or arrangements of parts described and shown.

I claim:

1. Apparatus for monitoring the integrity of a protective garment worn by a worker comprising:
   A) a one-piece protective garment that includes an electrically conductive layer and an insulating layer;
   B) a first electrical contact electrically connected with said conductive layer;
   C) an alarm circuit that includes
      (1) a second electrical contact electrically separated from said first electrical contact by said insulating layer,
      (2) an alarm element connected to said first and second electrical contacts, and
      (3) power means connected to said alarm element and to said first and second electrical contacts.

2. The apparatus defined in claim 1 wherein said first electrical contact is integral with said electrically conductive layer.

3. The apparatus defined in claim 2 wherein said second electrical contact is electrically connected to a worker wearing the protective garment.

4. The apparatus defined in claim 1 further including a second electrically conductive layer, said insulating layer being sandwiched between said electrically conductive layers.

5. The apparatus defined in claim 4 wherein said second electrical contact is electrically connected to said second electrically conductive layer.

6. The apparatus defined in claim 1 further including a second electrically insulating conductive layer, said electrically conductive layer being sandwiched between said electrically insulating layers.

7. The apparatus defined in claim 1 wherein said electrically conductive layer is impermeable to liquid.

8. The apparatus defined in claim 1 wherein said alarm circuit includes a current amplifying element that is biased to be cutoff when the protective garment is in a non-breached condition.

9. The apparatus defined in claim 8 wherein said first and second electrical contacts are spaced apart from each other at a maximum spacing of about 3/64th of an inch therebetween.

10. The apparatus defined in claim 1 wherein the protective garment includes a glove.

11. The apparatus defined in claim 1 wherein said alarm circuit further includes a pre-breach alarm activating means.

12. The apparatus defined in claim 11 wherein said pre-breach alarm activating means includes a sensitivity adjusting element in said alarm circuit.

13. In a system for continuously monitoring a protective garment for detecting and signalling the occurrence of a breach in such protective garment comprising:
   A) a unit including
      (1) a housing,
      (2) a power source,
      (3) an alarm device, and
      (4) a circuit for connecting said alarm device to said power source and which includes a current amplifier connected to said power source, said current amplifier having means for generating current when power is applied thereto in a particular manner; and
   B) normally open switch means for connecting said circuit to said alarm device when closed, said switch means being closed when the person's skin contacts some portion of a workpiece on which that person is working, said switch means including
      (1) a first contact element electrically connected with one side of said power source,
      (2) a second contact electrically connected to one side of said alarm element,
      (3) a current activated element associated with said switch means first contact to cause that switch means first contact to electrically contact said switch means second contact when power is applied to said current activated element in said particular manner to apply power from said power source to said alarm device,
      (4) a first electrical wire connecting another side of said alarm device to another side of said power source,
      (5) a first electrical contact element connected to said power source another side and mountable in electrical contact with the person,
      (6) a second electrical contact element connected to said current amplifier and to said power source one side and being mountable on the workpiece,
      (7) said protective garment being electrically insulating and being electrically interposed between the person and said electrically conductive workpiece and preventing formation of an electrically conductive path between said workpiece and said first electrical contact element when said protective garment is imperforate and permitting formation of an electrically conductive path between said workpiece and said first electrical contact element via any perforation in said protective garment, the formation of said electrically conductive path causing power from said power source to be applied to said current amplifier in said particular manner and activating said current amplifier, current associated with said activated current amplifier causing power from said power source to be applied to said alarm device to activate said alarm device, the improvement in combination therewith comprising:

said protective garment being one piece and having an electrically conductive layer in electrical contact with said first electrical contact and an insulating layer electrically interposed between said first and said second electrical contacts.

14. In a system for continuously monitoring a protective garment for detecting and signalling the occurrence of a breach in such protective garment comprising:

A) a unit including
(1) a housing,
(2) a power source,
(3) an alarm device, and
(4) a circuit for connecting said alarm device to said power source and which includes a current amplifier connected to said power source, said current amplifier having means for generating current when power is applied thereto in a particular manner;

B) normally open switch means for connecting said circuit to said alarm device when closed, said switch means being closed when the person's skin contacts some portion of a workpiece on which that person is working, said switch means including
(1) a first contact element electrically connected with one side of said power source,
(2) a second contact electrically connected to one side of said alarm element,
(3) a current activated element associated with said switch means first contact to cause that switch means first contact to electrical contact said switch means second contact when current is applied to said current activated element to apply power from said power source to said alarm device, (4) a first electrical wire connecting another side of said alarm device to another side of said power source,
(5) a first electrical contact element connected to said power source another side and mountable in electrical contact with the person,
(6) a second electrical contact element connected to said current amplifier and to said power source one side and being mountable on the workpiece,
(7) said protective garment being electrically insulating and being electrically interposed between the person and said electrically conductive workpiece and preventing formation of an electrically conductive path between said workpiece and said first electrical contact element when said protective garment is imperforate and permitting formation of an electrically conductive path between said workpiece and said first electrical contact element via any perforation in said protective garment, the formation of said electrically conductive path causing power from said power source to be applied to said current amplifier in said particular manner and activating said current amplifier, current associated with said current amplifier being applied to said normally open switch element and causing said normally open switch element to close, said normally open switch element connecting said power source to said alarm means when closed and causing power from said power source to be applied to said alarm device to activate said alarm device; and C) second current amplifying means for sensing if either said first electrical contact element or said second electrical contact element is not making proper electrical contact with said person or said workpiece respectively, the improvement in combination therewith comprising:

said protective garment being one piece and having an electrically conductive layer in electrical contact with said first electrical contact and an insulating layer electrically interposed between said first and said second electrical contacts.

* * * * *